(12) United States Patent  
Aydin

(10) Patent No.: US 11,298,294 B2  
(45) Date of Patent: *Apr. 12, 2022

(54) FLUID VALVE AND FLUID CONNECTION SYSTEM

(71) Applicant: PARKER HANNIFIN MANUFACTURING GERMANY GMBH & CO. KG, Bielefeld (DE)

(72) Inventor: Tolga Aydin, Bad Wimpfen (DE)

(73) Assignee: PARKER HANNIFIN MANUFACTURING GERMANY GMBH & CO. KG, Bielefeld (DE)

( * ) Notice: Subject to any disclaimer, the term of this patent is extended or adjusted under 35 U.S.C. 154(b) by 694 days.

This patent is subject to a terminal disclaimer.

(21) Appl. No.: 16/158,523

(22) Filed: Oct. 12, 2018

(65) Prior Publication Data

US 2019/0038510 A1 Feb. 7, 2019

Related U.S. Application Data

(63) Continuation of application No. 14/781,949, filed as application No. PCT/EP2014/056512 on Apr. 1, 2014, now Pat. No. 10,123,941.

(51) Int. Cl.
| | |
|---|---|
| *A61J 1/00* | (2006.01) |
| *A61J 1/22* | (2006.01) |
| *A61J 1/20* | (2006.01) |
| *A61M 39/10* | (2006.01) |

(Continued)

(52) U.S. Cl.  
CPC .............. *A61J 1/22* (2013.01); *A61J 1/2048* (2015.05); *A61J 1/2089* (2013.01); *A61J 1/2093* (2013.01);

(Continued)

(58) Field of Classification Search  
CPC ...... A61J 1/2096; A61J 1/2037; A61J 1/2089; A61J 1/1425; A61M 39/26; A61M 5/162  
See application file for complete search history.

(56) References Cited

U.S. PATENT DOCUMENTS

| 5,215,538 A | 6/1993 | Larkin |
| 5,280,876 A | 1/1994 | Atkins |

(Continued)

FOREIGN PATENT DOCUMENTS

| DE | 40 26 524 A1 | 3/1992 |
| DE | 10 2010 047 747 A1 | 4/2012 |

(Continued)

OTHER PUBLICATIONS

International Search Report, PCT/EP2014/056512, dated Oct. 23, 2014, 5 pgs.

(Continued)

*Primary Examiner* — Leslie R Deak  
(74) *Attorney, Agent, or Firm* — Paul D. Strain, Esq.; Strain & Strain PLLC

(57) ABSTRACT

The invention relates to a fluid valve and fluid connection system, comprising a casing having a chamber with a first internal connection element and a first external connection element; comprising a first movable valve element in the chamber; and comprising an actuating element which has a fluid communication system with a second internal connection element and a second external connection element; wherein the first internal connection element cooperates with the second internal connection element and the valve element to establish or block a fluid connection between the first and second external connection elements.

17 Claims, 5 Drawing Sheets

(51) Int. Cl.
  *A61M 5/162* (2006.01)
  *F16K 15/00* (2006.01)
  *A61M 39/26* (2006.01)
(52) U.S. Cl.
  CPC ............ *A61M 5/162* (2013.01); *F16K 15/00* (2013.01); *A61J 1/201* (2015.05); *A61J 1/2013* (2015.05); *A61J 1/2037* (2015.05); *A61J 1/2051* (2015.05); *A61J 1/2055* (2015.05); *A61J 1/2075* (2015.05); *A61M 39/26* (2013.01); *A61M 2039/1072* (2013.01)

(56) References Cited

U.S. PATENT DOCUMENTS

| | | | |
|---|---|---|---|
| 5,390,898 | A | 2/1995 | Smedley et al. |
| 5,578,059 | A | 11/1996 | Patzer |
| 10,123,941 | B2 * | 11/2018 | Aydin ................ F16K 15/00 |
| 2016/0030287 | A1 | 2/2016 | Aydin |

FOREIGN PATENT DOCUMENTS

| | | |
|---|---|---|
| EP | 1 454 650 A1 | 9/2004 |
| FR | 2 952 813 A1 | 5/2011 |
| WO | WO 93/20772 A1 | 10/1993 |
| WO | WO-9320772 A1 * | 10/1993 ............ A61M 5/162 |
| WO | WO 96/17646 A1 | 6/1996 |
| WO | WO 98/14163 A1 | 4/1998 |
| WO | WO 2008/022040 A1 | 2/2008 |

OTHER PUBLICATIONS

German Search Report, Appl. No. 10 2013 205 813.6, dated Aug. 23, 2013, 5 pgs.

Aydin; U.S. PTO Office Action, U.S. Appl. No. 14/781,949, dated Mar. 15, 2018, 8 pgs.

Aydin; U.S. PTO Notice of Allowance, U.S. Appl. No. 14/781,949, dated Jul. 13, 2018, 5 pgs.

* cited by examiner

ID SYSTEM

CROSS-REFERENCE TO RELATED PATENT APPLICATIONS

This application is a Continuation of U.S. application Ser. No. 14/781,949, filed Oct. 2, 2015, which is a National Stage of International Application No. PCT/EP2014/056512, filed Apr. 1, 2014, which is based upon and claims the benefit of priority from prior German Patent Application No. 10 2013 205 813.6, filed Apr. 2, 2013, the entire contents of all of which are incorporated herein by reference in their entirety.

TECHNICAL FIELD

The invention relates to a fluid valve and fluid connection system, in particular for connecting vessels and for producing a controlled fluid connection between vessels and/or elements attached to the fluid valve and fluid connection system.

PRIOR ART

In particular in the medical field of application, it is known in the prior art that liquid agents or drugs are received from a storage vessel by means of injection and are administered to patients either mixed with other liquids or directly.

It is also known that different agents, such as liquids and/or solids, for example as powder or the like, from two different storage vessels are mixed with one another by transferring one agent from a first storage vessel into a second storage vessel, in which the second agent is stored, and by then mixing, the agents in the second storage vessel. For this purpose one of the agents by way of example is a liquid that is to be transferred from the first storage vessel into the second storage vessel. By means of a connection element, a fluid connection thus can be produced between the two storage vessels. Here, however, the liquid is transferred only moderately to not at all.

If, by contrast, a negative pressure is produced in the first storage vessel, the liquid is thus suctioned from the first storage vessel into the second storage vessel following production of the fluid connection between the two storage vessels. If the second agent in the second storage vessel is a powder to be mixed with the liquid, the sudden suction of the liquid thus poses a problem because it may also lead in some circumstances to non-uniform mixing or clump formation, which may make the mixture unusable. In the case of expensive drugs this is to be avoided wherever possible.

DISCLOSURE OF THE INVENTION, PROBLEM, SOLUTION, ADVANTAGES

The object of the invention is to create a fluid valve and fluid connection system that allow a reliable fluid connection and yet also a controlled fluid flow between two vessels.

This is achieved with the features of claim 1.

An advantageous exemplary embodiment of the invention relates to a fluid valve and fluid connection system comprising a housing having a receiving chamber with a first internal connection element and with a first external connection element, comprising a first movable valve element arranged in the receiving chamber, and comprising an actuating element, which has a fluid communication system with a second internal connection element and with a second external connection element, wherein the first internal connection element cooperates with the second internal connection element and the valve element in order to establish or to block a fluid connection between the first and the second external connection elements. Here, two media, such as agents, can be selectively combined by means of the fluid connection producible in a controlled manner, such that a selective mixing can take place.

Here, it is expedient when the actuating element can be moved relative to the housing and can adopt a first position, in which the fluid connection between the first and the second external connection elements is blocked, and can adopt a second position, in which the fluid connection between the first and the second external connection elements is established. By means of the selective movement of the actuating element from a first position into a second position, a fluid connection is produced by moving one element of the system. If this movement is selectively hindered, the production of the fluid connection may thus also be hindered or, when the fluid connection is allowed, may thus also be selectively produced.

It is also advantageous when the actuating element has means that cooperate with means of the housing in order to define the first and the second positions. This is advantageous when a predefined position is to be adopted or the adoption of this position is to be prevented.

Here, it is expedient when the means of the actuating element have at least one arm, which has at least one radially inwardly oriented protrusion, and wherein the means of the housing are grooves formed in a housing wall. Here, the grooves are preferably oriented in the radial direction so that the at least one protrusion can engage with one of the grooves. By displacing the actuating element in the axial direction the engagement can be swapped from one groove into the other groove from the first position to the second position. A defined displacement is thus ensured.

Here, it is expedient when the grooves are arranged spaced apart from one another in the axial direction of the housing. The distance between the two positions is thus defined.

It is also expedient when the at least one arm is arranged in the first position in such a way that the at least one protrusion engages with one of the grooves and the at least one arm is arranged in the second position in such a way that the at least one protrusion engages with another of the grooves. The movement from the first position to the second position is thus defined in the spacing.

It is particularly advantageous when a blocking element is provided, which when in a first position prevents the actuating element from adopting the second position and which when in a second position allows the actuating element to adopt the second position. Here, the blocking element is used as a means for preventing a fluid connection. This allows the system according to the invention to be attached at both external connection elements to a vessel, such as a storage vessel, without thus producing a fluid connection. Only by moving or removing the blocking element may the actuating element be moved, which produces the fluid connection.

It is particularly advantageous when the blocking element is an open ring element, which grasps around the housing and prevents the actuating element from adopting the second position in that the position of the means of the actuating element is limited in such a way that the at least one protrusion cannot engage with the groove associated with the second position. Due to the shaping, the blocking element may be introduced favorably, such that it fixes the actuating element in a position or prevents the actuating element from adopting the second position.

Here, it is expedient when the housing is provided with fastening means in order to fasten the housing to a second storage vessel. The housing may thus be fixedly attached to the storage vessel so that no unintentional leaks or agent losses occur.

It is also expedient when the housing is provided with the second external connection element in order to establish a fluid connection to the second storage vessel.

It is furthermore expedient when the actuating element is provided with fastening means in order to fasten the housing to a first storage vessel.

It is also advantageous when the actuating element is provided with the first external connection element in order to establish a fluid connection to the first storage vessel.

Here, it is advantageous when the fastening means are formed in the manner of detent arms. It is thus possible to attain a connection without tools, which connection can also be easily released again manually.

It is also expedient when the first and/or the second connection element is/are formed in the manner of a hollow cannula or as a hollow pin. The storage vessel having a cover thus may be pierced in order to produce the fluid connection.

It is particularly advantageous when the first internal connection element is a hollow-cylindrical connecting piece and the second internal connection element is a hollow-cylindrical connecting piece, which engage with one another when moved between the first position and the second position. A reliable fluid connection can thus be produced.

It is also expedient when the second internal connection element is a hollow-cylindrical connecting piece that, when moved between the first position and the second position, acts on the valve element. The valve element is thus automatically actuated upon actuation of the actuating element.

It is also expedient when the valve element in the first position of the actuating element blocks the fluid connection between the first and the second external connection elements and the valve element in the second position of the actuating element enables the fluid connection between the first and the second external connection elements.

It is particularly advantageous when the valve element has an approximately cylindrical region with spring arms protruding away from the cylindrical region.

Here, it is also advantageous when the valve element is arranged with its approximately cylindrical region in the first internal connection element, wherein the spring arms are each supported on an inner wall of the housing.

Further advantageous embodiments are described by the following description of the drawings and also by the dependent claims.

BRIEF DESCRIPTION OF THE DRAWINGS

The invention will be explained in greater detail hereinafter on the basis of at least one exemplary embodiment with reference to the drawings, in which.

PREFERRED EMBODIMENT OF THE INVENTION

Figure 1:
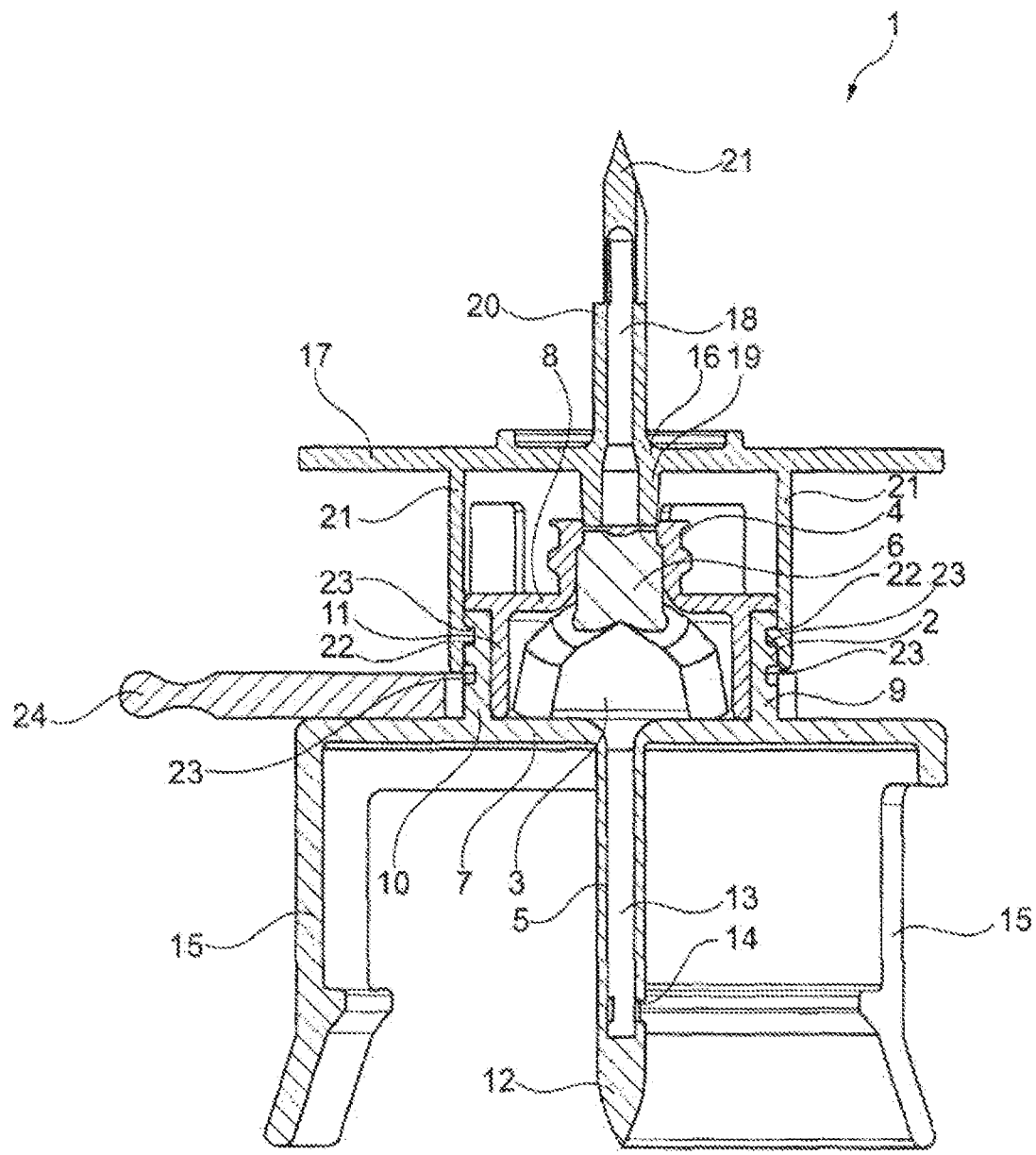
FIG. 1 shows a section through an exemplary embodiment of a fluid valve and fluid connection system according to the invention in a first operating position.

FIG. 1 shows a fluid valve and fluid connection system 1 comprising a housing 2 having a receiving chamber 3 arranged in the housing 2 with a first internal connection element 4 and with a first external connection element 5. Here, a fluid connection between the first internal connection element 4 and the first external connection element 5 can be established or blocked in that a valve element 6 is arranged in the receiving chamber 3 or in the first internal connection element 4 in order to allow or to block a fluid connection.

The housing 2 consists of a bottom-side wall 7, an opposing top-side wall 8 and also a substantially annular-cylindrical wall 9, which connects the bottom-side wall 7 to the top-side wall 8.

In the exemplary embodiment of FIG. 1 the annular wall 9 is double-walled, wherein one wall 10 protrudes away from the bottom-side wall 7 in the axial direction and one wall 11 protrudes away from the top-side wall 8 in the axial direction in such a way that the two walls 10, 11 are arranged radially one inside the other and can be connected to one another. The wall 10 by way of example may thus be connected to the wall 11, preferably welded or adhesively bonded for example.

In a further exemplary embodiment one of the walls 10, 11 may also be spared, such that the remaining one wall 10, 11 is then formed in one piece either with the bottom-side wall 7 or the top-side wall 8 and is connected to respective other wall 8, 7.

In a further exemplary embodiment the wall 9 may also be formed as a separate element and may be connectable both to the bottom-side wall 7 and to the top-side wall 8.

The first internal connection element 4 is preferably a hollow-cylindrical connecting piece protruding away from the top-side wall 8 in the axial direction. The first external connection element 5 is preferably a hollow cannula or a hollow pin, which protrudes in the axial direction away from the bottom-side wall 7. Here, the first external connection element 5 preferably protrudes in the opposite direction away from the wall 7 compared with the direction in which the first internal connection element 4 protrudes away from the top-side wall 8.

The first external connection element 5, as can be seen in FIG. 1, is formed as a hollow cannula or as a hollow pin, wherein the pin or the cannula is pointed at its front end region 12 so as to be able to be pushed through a cover of a storage vessel. A fluid path 13 is provided in the hollow pin or in the hollow cannula and may establish a fluid connection between the receiving chamber 3 and a storage vessel, wherein the discharge opening 14 of the first external connection element 5 as a hollow pin or as a hollow cannula is preferably arranged on a side wall of the hollow cannula or of the hollow pin. As a result, when a fluid flows from the receiving chamber 3 through the fluid path 13 and the discharge opening 14, the fluid flow exits in the radial direction and preferably flows against a side wall of the storage vessel. From there, the fluid or agent may flow for example along the wall to the bottom of the storage vessel. This ensures an improved mixing of the fluids or agents to be mixed.

The bottom-side wall 7 has, on the radial end regions thereof, fastening means 15, which are formed in the manner of detent hooks, in order to be able to reliably connect a storage vessel to the fluid valve and fluid connection system.

In order to connect a storage vessel to the system according to the invention by means of the fastening elements 15, a storage vessel may be slid from below in FIG. 1 toward the pin of the first external connection element 5, such that the vessel at the same time is secured by means of the fastening elements formed as detent hooks.

The system 1 according to the invention also comprises an actuating element 16, which has a base plate 17, which carries a fluid channel 18 formed on one side of the base plate 17 by the second internal connection element 19 and on the other side of the base plate by the second external connection element 20.

The second internal connection element 19 is formed by a pipe socket, which is formed and arranged substantially coaxially with the first internal connection element 4. The second external connection element 20 is preferably formed as a hollow pin, which on the front side of the hollow pin has an opening 21 in order to allow a fluid connection between the second external connection element 20 and the second internal connection element 19 when a cover of a storage vessel has been pierced.

The actuating element 16 also has means that cooperate with means of the housing in order to define the positioning of the actuating element 16 relative to the housing 2. At least one arm or a plurality of arms 21 is/are provided as actuating-element-side means and extends/extend in the axial direction and has/have, at the end regions thereof, protrusions 22 extending in the radial direction. These protrusions 22 may engage with grooves 23 in the wall 9 of the housing, said grooves preferably being formed circumferentially in the wall 9. Here, the grooves 23 are spaced apart from one another in such a way that, when the protrusions 22 engage with the first groove 23, i.e. the uppermost groove 23, the actuating element 16 is arranged in its first position, and, when the protrusions 22 engage with the second, lower groove 23, the actuating element 16 is arranged in its second position.

A blocking element 24 is also provided, which, when in its target position, merely allows the actuating element 16 to be arranged in the first position thereof, because the protrusions 22 are blocked from adopting the second position in the groove 23.

In FIG. 1 it can be seen that the protrusions 22 of the arms 21 are arranged in the upper of the two grooves 23, and therefore the second internal connection element 19 does not engage or only slightly engages with the opening of the first internal connection element 4 and does not act on or only slightly acts on the movable valve element 6, such that the fluid connection between the first external connection element 5 and the second external connection element 20 is blocked.

Figure 2:
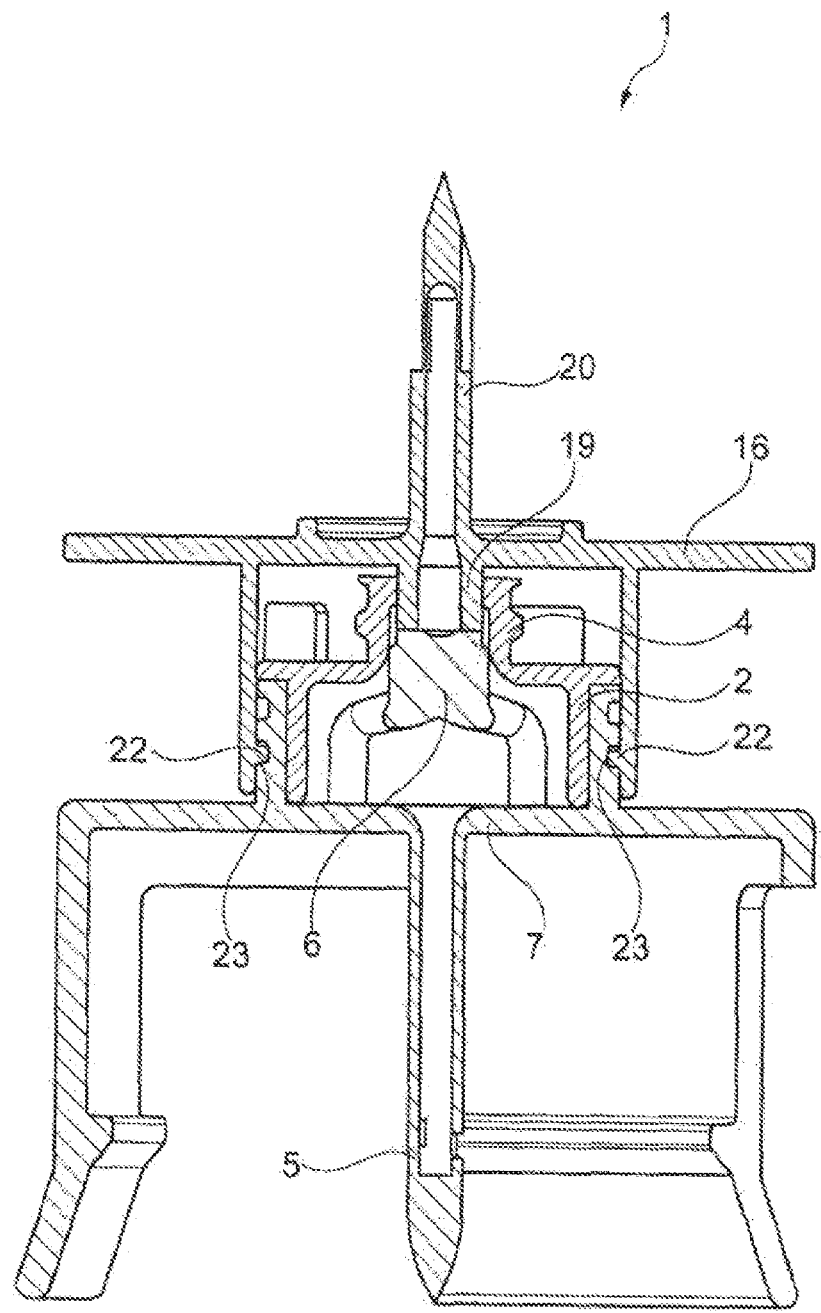
FIG. 2 shows a section through an exemplary embodiment of a fluid valve and fluid connection system according to the invention in a second operating position.

In FIG. 2 the actuating element 16 is moved relative to the housing 2 in such a way that the protrusions 22 engage with the lower of the two grooves 23 and the actuating element adopts its second position relative to the housing. In this second position the second internal connection element 19 engages with the first internal connection element 4 and acts on the valve element 6 in such a way that the valve element 6 is deformed or moved in the direction of the wall 7 in order to establish a fluid connection between the first external connection element 5 and the second external connection element 20.

Figure 3:
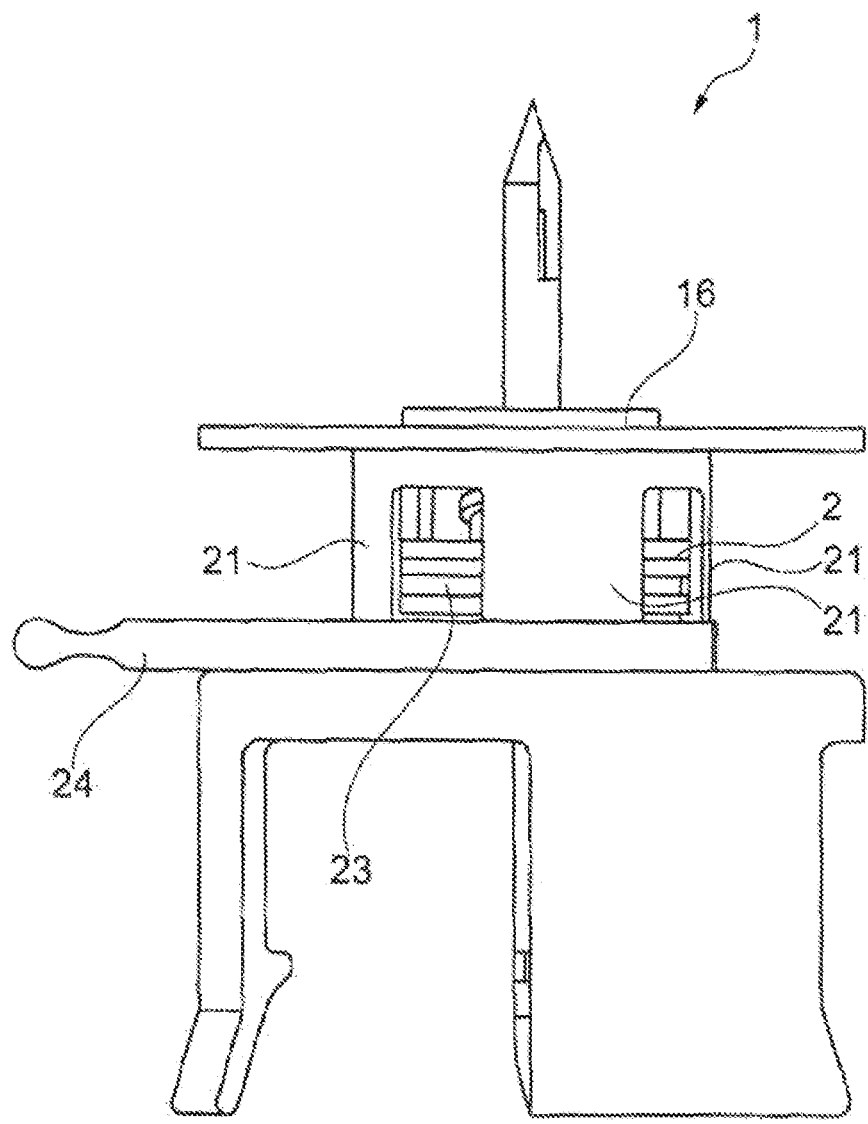
FIG. 3 shows a side view of the fluid valve and fluid connection system according to the invention in the first operating position.

FIG. 3 shows a view of the fluid valve and fluid connection system 1 according to the invention with the housing 2 and the actuating element 16, wherein it can be seen that the arms 21 are formed as arms curved in the manner of a segment of a circle, which arms have, on their inner wall, the protrusions 22, which can engage with the grooves 23. The blocking element 24 is formed as an annular element with an open ring, such that it can be removed from the assembly in a lateral or radial direction in order to enable the movability of the actuating element 16 in the axial direction between the first and the second positions.

Figure 4:
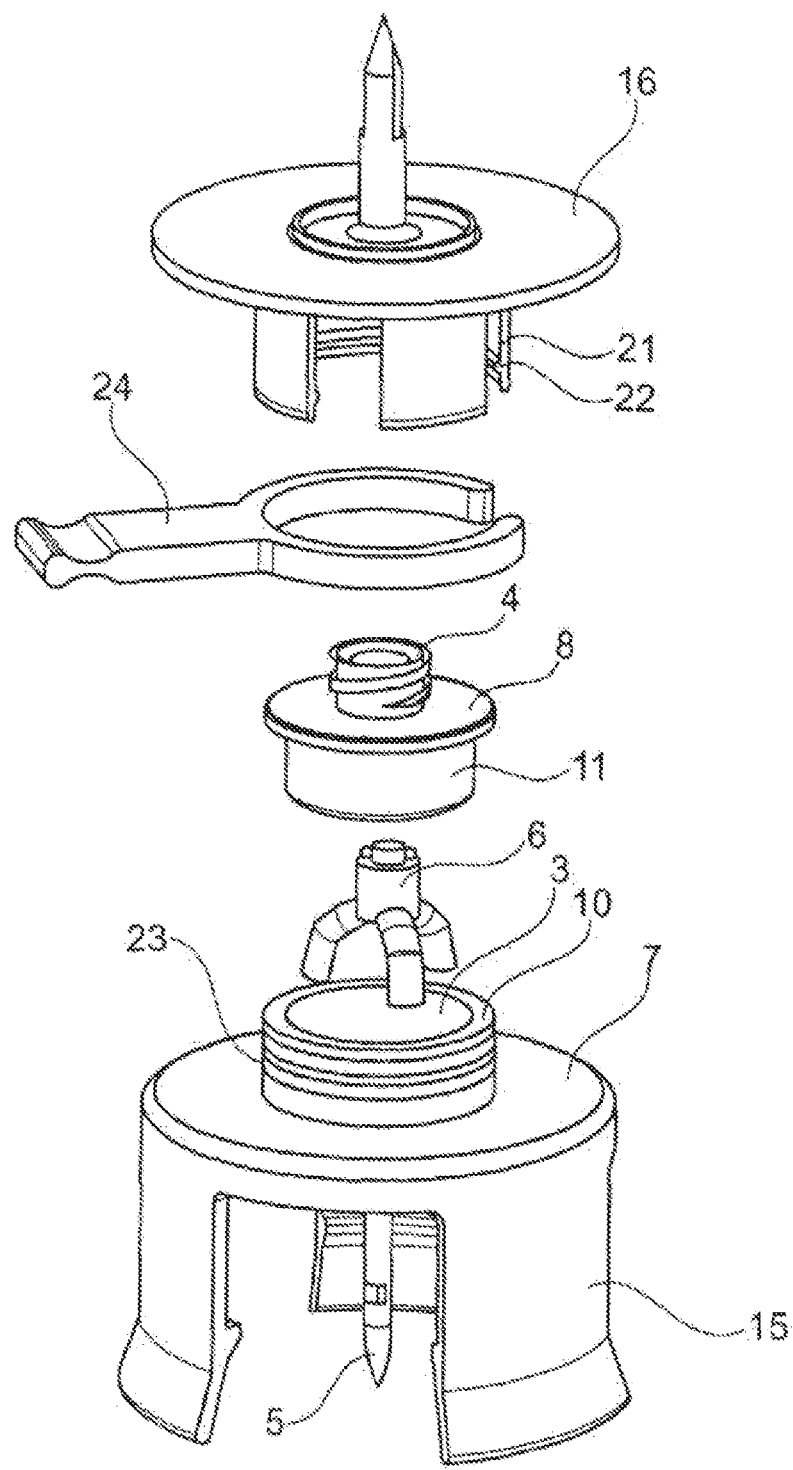
FIG. 4 shows an exploded illustration of the fluid valve and fluid connection system according to the invention.

FIG. 4 shows the system according to the invention in an exploded illustration. It can be seen that the bottom-side wall 7 can be formed in one piece with the wall 10, which carries the grooves 23, wherein the movable valve element 6 also can be inserted into the receiving chamber 3.

The element with the top-side wall and the sub-wall 11 and the first internal connection element 4 can then be arranged in the receiving chamber 3 and can be connected in a sealed manner. The actuating element 16 can then be placed onto the corresponding system, such that the actuating element, with intermediate insertion of the blocking element 24, can adopt merely the first position, such that the protrusions 22 can engage merely with the upper of the two grooves 23 in order to fix the actuating element 16 in the first position. For this purpose the blocking element 24 is formed as an open ring with grip elements, such that the open ring can be slid externally over the housing 2 in order to limit the axial position of the actuating element 16 relative to the housing 2.

The valve element 6 has a cylindrical region, from which spring arms protrude away downwardly. Here, the cylindrical region is formed advantageously in one piece with the spring arms, and the spring arms protrude radially outwardly and downwardly away from the cylindrical region at an angle from approximately 30° to 60°, such as preferably 45°, to the vertical. The spring arms may be straight or alternatively may also be angled.

The straight spring arms, with the presence of three spring arms, form an arrangement according to an edge arrangement of a tetrahedron. For the angled spring arms approximately the same is true for the parts of the spring arms adjoining the cylindrical region.

At the upper end of the cylindrical region of the spring element a cross-shaped or star-shaped groove structure is formed and is used to ensure a fluid connection between the first and the second external connection elements.

In the positions of the valve element 6 shown in FIGS. 1 and 2, a fluid connection between the first and the second external connection elements is provided or is closed and sealed off. If the cylindrical region of the valve element is acted on and slid downwardly, the spring arms will thus be supported in the corners of the receiving chamber or on the bottom thereof and will be resiliently deformed. This will occur until a fluid connection is present.

If the element acting on the valve element is removed again from the internal connection element 4, the resilient formable valve element 6 relaxes again, and the cylindrical region is slid upwardly again, such that the internal connection element 4 is sealed again.

The system, i.e. the housing, the actuating element and/or the blocking element, is preferably formed from polycarbonate. It is also advantageous when the valve element is formed from a rubber, such as LSR (liquid silicone rubber).

Figure 5:
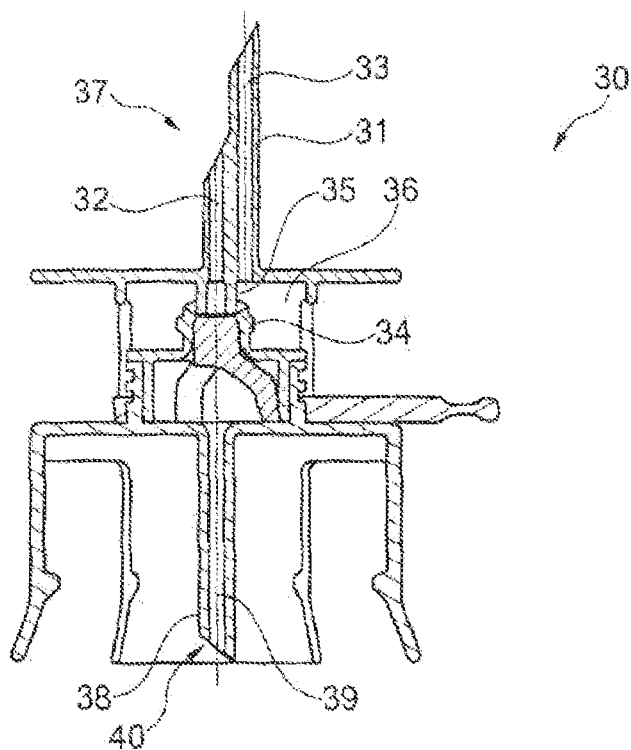
FIG. 5 shows a section through a further exemplary embodiment of a fluid valve and fluid connection system according to the invention.
Figure 6:
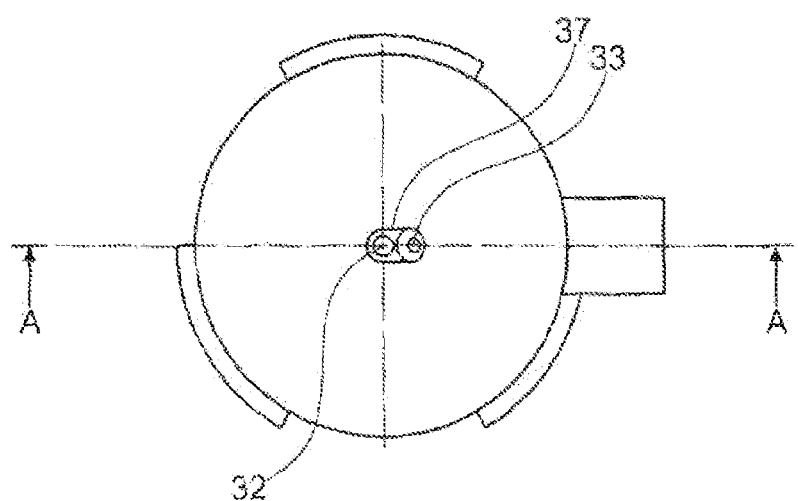
FIG. 6 shows a view from above according to FIG. 5.

FIGS. 5 and 6 show a further exemplary embodiment of the invention, in which, compared with the exemplary embodiment shown in FIGS. 1 to 4, the connection elements have a modified form. The other features are fundamentally unchanged and therefore will not be described in greater detail. Reference is made in this regard to the description of FIGS. 1 to 4.

In FIG. 5 the first external connection element 31 of the fluid valve and fluid connection system 30 is formed as a double channel having the channels 32, 33. Here, the channel 32 is shorter than the channel 33. The upper end regions of the channels are optionally chamfered here, wherein the upper end region of the channel 33 forms a tip suitable for being pushed through a closure cap of a vessel. The upper end region of the channel 32 is also advantageously chamfered to this effect.

The channel 32 leads at its lower end region into the first internal connection element 34, wherein a connecting piece 35 of the channel 32 engages with the first internal connection element 34. The channel 33 has, at its lower end region, an opening, which lies beside the connecting piece 35 and which leads into the chamber 36, which is open to the outside.

In the case in which a liquid is in the vessel connected to the pin 37 and a vacuum prevails in the vessel connected by means of the pin 38, this double-channel structure causes the liquid to be sucked from one vessel into the second vessel, wherein the liquid flows through the channel 32. During this process air is suctioned through the channel 33 into the first vessel, which promotes the fluid flow from the first vessel to the second vessel, because no negative pressure can form in the first vessel.

FIG. 6 shows the two channels 32, 33 in the pin 37 from above.

The pin 38, as second external terminating element, is formed as a downwardly open conduit with a channel 39 having a chamfered portion 40 at the end. A vessel arranged at the lower region of the fluid valve and fluid connection system 30 is preferably fluidically connected to the pin 38.

It is also preferable when a filter is provided in the first channel 32 and/or in the second channel 33. This filter by way of example may be a paper filter or the like, which is arranged in one of the channels 32, 33 or is located upstream or downstream thereof. By way of example, a filter could thus be arranged in the connecting piece 35.

LIST OF REFERENCE SIGNS 1 fluid valve and fluid connection system
2 housing
3 receiving chamber
4 first internal connection element
5 first external connection element
6 valve element
7 wall
8 wall
9 wall
10 sub-wall
11 sub-wall
12 end region
13 fluid path
14 discharge opening
15 fastening element
16 actuating element
17 base plate
18 fluid channel
19 second internal connection element
20 second external connection element
21 arm
22 protrusion
23 groove
24 blocking element

The invention claimed is:

1. A fluid valve and fluid connection system comprising
a housing having a receiving chamber with a first internal connection element and with a first external connection element,
a first movable valve element arranged in the receiving chamber, and
an actuating element, which has a fluid communication system with a second internal connection element and with a second external connection element,
wherein the first internal connection element cooperates with the second internal connection element and the valve element to open or to block a fluid connection between the first and the second external connection elements,
wherein the actuating element comprises at least one arm, wherein the at least one arm has at least one radially inwardly oriented protrusion, and wherein the housing comprises at least two grooves formed in a housing wall that are complimentary to the at least one radially inwardly oriented protrusion, wherein the grooves are arranged spaced apart from one another in the axial direction of the housing,
wherein the actuating element is configured to be movable relative to the housing between a first position and a second position, wherein in the first position the fluid connection between the first and the second external connection elements is blocked, wherein in the first position the at least one arm is arranged such that the at least one radially inwardly oriented protrusion engages with a first groove associated with the first position, wherein in the second position the fluid connection between the first and the second external connection elements is open, wherein in the second position the at least one arm is arranged such that the at least one radially inwardly oriented protrusion engages with a second groove associated with the second position.

2. The fluid valve and fluid connection system as claimed in claim 1,
wherein the actuating element is configured to be movable relative to the housing between a first position and a second position, wherein in the first position the fluid connection between the first and the second external connection elements is blocked, wherein in the second position the fluid connection between the first and the second external connection elements is open.

3. The fluid valve and fluid connection system as claimed in claim 1,
wherein the actuating element has means that cooperate with means of the housing in order to define the first and the second positions.

4. The fluid valve and fluid connection system as claimed in claim 1,
further comprising a blocking element, wherein the blocking element is configured to be movable from a blocking position to a nonblocking position, wherein when the blocking element is in the blocking position, the blocking element prevents the actuating element from adopting the second position, wherein when the blocking element is in the nonblocking position, the blocking element allows the actuating element to adopt the second position.

5. The fluid valve and fluid connection system as claimed in claim 4,
wherein the blocking element is an open ring element, which grasps around the housing and prevents the actuating element from adopting the second position by limiting the movement of the actuating element in such a way that the at least one protrusion cannot engage with the second groove associated with the second position.

6. The fluid valve and fluid connection system as claimed in claim 1,
wherein the housing comprises a first fastener configured to fasten the fluid vale and fluid system to a first storage vessel.

7. The fluid valve and fluid connection system as claimed in claim 6,
wherein the housing further comprises the first external connection element, which is configured to establish a fluid connection to the first storage vessel.

8. The fluid valve and fluid connection system as claimed in claim 6,
wherein the first fastener is formed in the manner of detent arms.

9. The fluid valve and fluid connection system as claimed in claim 1,
wherein the actuating element comprises a second fastener configured to fasten the actuating element to a second storage vessel.

10. The fluid valve and fluid connection system as claimed in claim 9,
wherein the actuating element further comprises the second external connection element, which is configured to establish a fluid connection to the second storage vessel.

11. The fluid valve and fluid connection system as claimed in claim 10,
wherein the second external connection element is formed with two channels.

12. The fluid valve and fluid connection system as claimed in claim 1,
wherein the first or the second external connection element is formed in the manner of a hollow cannula.

13. The fluid valve and fluid connection system as claimed in claim 1,
wherein the first internal connection element is a hollow-cylindrical connecting piece and the second internal connection element is a hollow-cylindrical connecting piece, which engage with one another when moved between the first position and the second position.

14. The fluid valve and fluid connection system as claimed in claim 1,
wherein the second internal connection element is a hollow-cylindrical connecting piece which, when moved between the first position and the second position, acts on the valve element.

15. The fluid valve and fluid connection system as claimed in claim 14,
wherein the valve element in the first position of the actuating element blocks the fluid connection between the first and the second external connection elements and the valve element in the second position of the actuating element allows the fluid connection between the first and the second external connection elements.

16. The fluid valve and fluid connection system as claimed in claim 1,
wherein the valve element has an approximately cylindrical region with spring arms protruding away from the cylindrical region.

17. The fluid valve and fluid connection system as claimed in claim 16,
wherein the valve element is arranged with its approximately cylindrical region in the first internal connection element such that the approximately cylindrical region seals the first internal connection element against the second internal connection element, wherein the spring arms are each supported on an inner wall of the housing.

* * * * *